United States Patent [19]
Kassel

[11] Patent Number: 4,997,367
[45] Date of Patent: Mar. 5, 1991

[54] DENTAL MATRIX

[76] Inventor: Larry I. Kassel, 1347 Hickory Hollow Dr., Flint, Mich. 48532

[21] Appl. No.: 351,386

[22] Filed: May 15, 1989

[51] Int. Cl.$^5$ ............................................. A61C 5/04
[52] U.S. Cl. ...................................... 433/39; 433/226
[58] Field of Search ................. 433/39, 40, 217.1, 226

[56] References Cited

U.S. PATENT DOCUMENTS

| | | | |
|---|---|---|---|
| 2,310,448 | 2/1943 | Leib | 433/39 |
| 2,611,182 | 9/1952 | Tofflemire | 433/39 |
| 2,646,622 | 7/1953 | Christie et al. | 433/39 |
| 2,674,801 | 4/1954 | Trangmar | 433/39 |
| 3,421,222 | 1/1969 | Newman | 433/39 |
| 4,226,593 | 10/1980 | Cohen et al. | 433/217 |
| 4,514,174 | 4/1985 | Dougherty et al. | 433/226 |
| 4,718,849 | 1/1988 | von Weissenfluh et al. | 433/39 |

FOREIGN PATENT DOCUMENTS 453283   9/1936   United Kingdom .................. 433/39

OTHER PUBLICATIONS

Paper entitled: Adverstising for Hawe-Neos Dental Cervicalfoil.

*Primary Examiner*—Cary E. Stone
*Attorney, Agent, or Firm*—Gifford, Groh, Sprinkle, Patmore & Anderson

[57] ABSTRACT

A method and apparatus for use in restoration procedures for teeth. The apparatus includes a matrix having a facial portion extending between a pair of wings. The facial portion has an anatomically contoured inner surface which extends between a pair of corners. The wings of the matrix are affixed together by an adhesive strip. A tapered flange extends outwardly from the facial portion for insertion between the gingiva and tooth to permit introduction of restorative material in the gingival and/or subgingival area. The matrix is formed of clear material to permit viewing of the restorative material during the procedure.

14 Claims, 2 Drawing Sheets

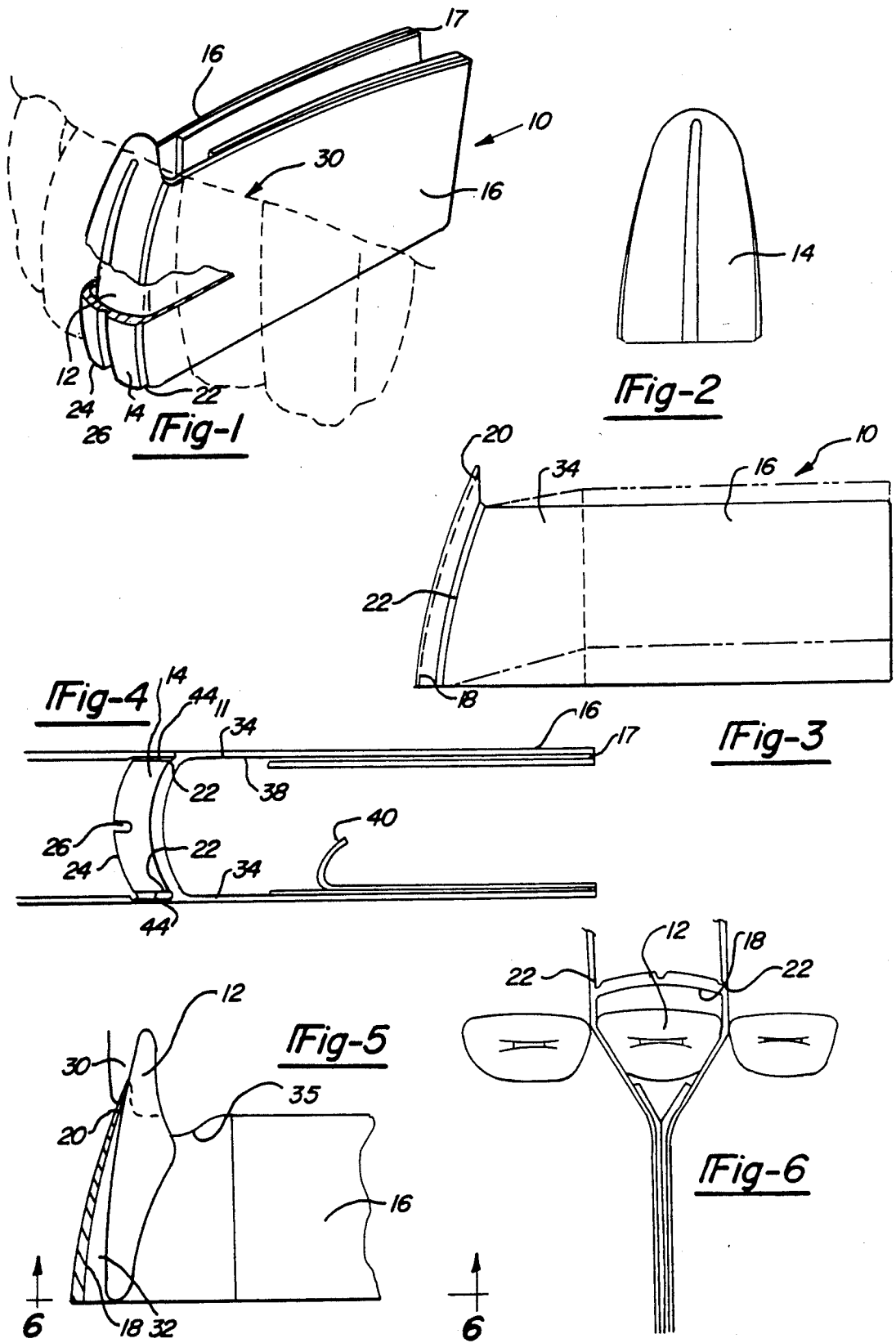

DENTAL MATRIX

BACKGROUND OF THE INVENTION

I. Field of the Invention

The present invention relates to a dental matrix, and more particularly to a dental matrix for use in restoration of a tooth.

II. Description of the Prior Art

The application of a restorative material to a patient's tooth for cosmetic and curative purposes is known. Typical methods of applying restorative material are, cementing prefabricated veneers to a surface of the tooth, bonding veneers or coatings of composite material to a surface of the tooth or filling voids or cavities with restorative material and the like.

Veneers or coatings of composite restorative may be applied for reconstructing teeth or for restoring or masking defects such as developmental abnormalities and fluorosis stains.

The surface of a damaged tooth may be restored by applying a composite restorative resin such as Heliosit or Silux to the surface and curing the material. In order to maintain proper spacing between the tooth being restored and adjacent teeth, the dentist may insert a Mylar strip encircling the tooth and restorative resin during the curing step.

A decayed portion of a tooth may be restored by mounting a celluloid crown form to a tooth and injecting restorative material into the cavity or void. However, such crown forms are frequently too thick to be positioned interproximally to maintain proper spacing. After the restorative resin is cured, the dentist contours, shapes, and polishes the restorative material so as to produce an appearance of a properly formed and colored natural tooth. However, considerable skill and time on the part of the dentist is required to produce a proper form and an attractive appearance to the coating of the restorative material. Additionally, it is difficult to control and observe the restorative material within the crown form resulting in undesired voids in the restorative material after curing.

It is also known to form a prefabricated veneer of porcelain or composite material over a dental cast or model for bonding to the surface of a tooth. As is disclosed in U.S. Pat. No. 4,226,593 to Cohen et al, a veneer blank is ground and shaped by a lab technician using a dental cast of the patient's teeth. The veneers are then encompassed by a flexible mold for removal from the dental cast and transferred in proper orientation to be secured on the patient's teeth. However, this method requires preparation of special molds and dental casts. As a result, this method is quite time consuming and costly.

Thus, it would be desirable to have a method and apparatus which would greatly reduce the amount of time, skill, and expense of applying coverings such as restorative materials and veneers to teeth.

SUMMARY OF THE INVENTION

The present invention thus provides a method and apparatus for the application of restorative material to damaged, decayed, or abnormally formed teeth. The apparatus includes a matrix having a facial portion extending between a pair of wings. The facial portion has a contoured inner surface extending between a pair of corners and a tapered flange. The inner surface is anatomically contoured in the shape of a desired labial surface. The anatomically contoured inner surface is positioned opposite the labial surface of the tooth by the pair of wings. The wings extend interproximally and are fastened about the tooth by adhesive strips affixed to at least one of the pair of wings. The matrix, so positioned, provides a mold for restorative material. The matrix may be used during the installation of a preformed veneer on the tooth to isolate the tooth during preparation and etching steps as well as maintaining the proper interproximal spacing.

The tapered flange extends outwardly to permit insertion of the inner surface of the matrix subgingivally and thereby permit adaptation of restorative material at the gingival and/or subgingival aspect of the tooth.

The matrix is formed of a clear material to allow for the use of light curing material and for observation of the restorative material. The matrix, thus, may be used as a form for shaping the restorative material, thereby resulting in a proper contour, requiring less skill of the part of the dentist to perform the shaping, and drastically reducing the finishing and polishing time. The matrix may be used during the bonding of restorative material in the repair of decayed teeth. The device permits proper interproximal spacing and gingival and/or subgingival adaptation of restorative material.

The present invention is primarily for use in composite resin bonding procedures. It is designed to aid the dentist or technician in accomplishing this procedure more quickly, accurately, and with more consistent results. It requires less finishing, trimming, and polishing time of the restoration. It also allows multiple teeth to be bonded simultaneously, while still allowing for proper interproximal contour and spacing. The present invention also allows for the matrix to be held in place about the tooth by itself. Secondarily, the present invention will be useful for many other restorative procedures, particularly those in which composite resin restorative materials are used and those in which preformed veneers are used.

BRIEF DESCRIPTION OF THE DRAWING

A better understanding of the present invention will be had upon reference to the following detailed description, when read in conjunction with the accompanying drawing, wherein like reference characters refer to like parts throughout the several views in which:

FIG. 1 is a perspective view of the device in position on a tooth according to the invention;

FIG. 2 is a front view of the matrix according to the invention:

FIG. 3 is a side view of the matrix according to the invention;

FIG. 4 is a top view of a first alternative embodiment of the matrix according to the invention;

FIG. 5 is a cross-sectional view of the matrix along lines 6—6;

FIG. 6 is a bottom view of the first alternative embodiment of the matrix about a tooth;

DETAILED DESCRIPTION OF THE PREFERRED EMBODIMENT

Figure 7:
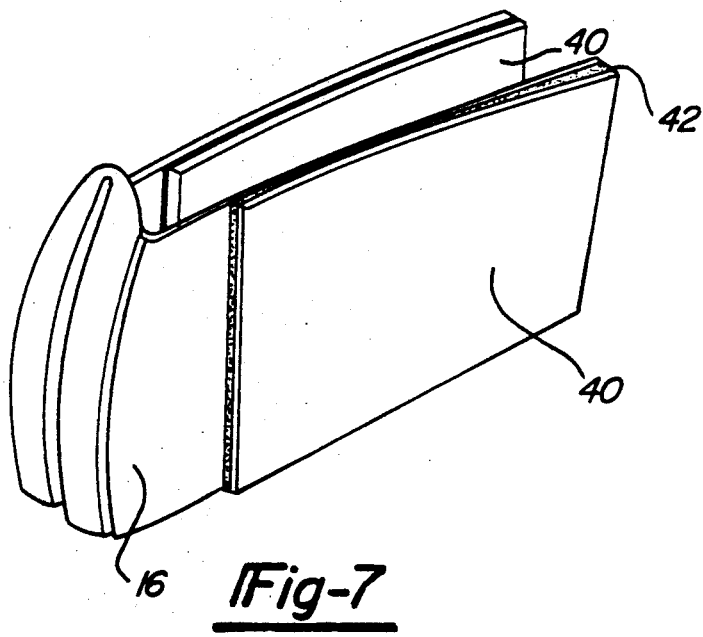
FIG. 7 is a perspective view of a second alternative embodiment of the matrix according to the invention.

As best shown in FIG. 1, an apparatus, such as a matrix 10, is shown for restoration of a tooth 12. The matrix 10 has a facial portion 14 extending between a pair of wings 16. Each of the pair of wings 16 has an adhesive material 17 on an inner surface 18 for attaching the pair of wings 16 together to secure the matrix to the tooth 12, as set forth below and best shown in FIG. 6. The matrix is formed of a suitable clear moldable material such as a polymer. The clear material permits curing of photosensitive compounds by visible light. As set forth below, the wings are formed with a thin cross section and are flexible. The facial portion 14 has a thicker cross section than the wings in order to resist deformation.

The facial portion 14 of the matrix has a contoured inner surface 18 and tapered flange 20. As shown in FIG. 6, the inner surface 18 extends between a pair of corner grooves 22 formed between the facial portion and the pair of wings 16. The inner surface 18 is anatomically contoured to have a surface complementary to a desired labial surface which is to be formed on the tooth. The inner surface 18 is formed to provide a mold for composite restoration material 32 as shown in FIG. 5. Because of the variety of sizes and shapes of human teeth, a number of matrices having different sized and shaped inner surfaces will be formed to properly accommodate differed sized and shaped teeth. The matrix will be formed in a suitable manner, such as molding, to provide an inner surface having a specific, predetermined anatomical contour and size.

The facial portion 14 has a thickness sufficient to maintain the predetermined anatomical contour of the inner surface 18 when the wings 16 are affixed together. The facial portion 14 is provided with an outer surface 24 which may be provided with a center groove 26, as shown in FIGS. 1 and 2. The center groove 26 extends vertically on the outer surface corresponding generally with the width "W" of the pair of wings so as not to extend on the flange 20 to irritate gingival tissue 30. The center groove 26 thus formed permits the facial portion to bend slightly along the groove when the wings are pulled and secured tightly against the lingual surface of the tooth 12. In this manner, the radius of curvature of the inner surface 18 can be altered to narrow the distance between the pair of corner grooves 22 if the inner surface is wider than desired to be formed on the tooth, as is discussed more fully below. The pair of corner grooves 22 are formed at the juncture of each wing and the facial portion of the matrix 10 to permit the wings to flexibly bend as desired to permit the wings to extend along the proximal surfaces of the tooth at the desired angle. Any excess restorative material is forced midfacially and extruded incisially from the matrix, resulting in a minimal amount of finishing necessary.

The tapered flange 20 extends outwardly beyond the pair of wings 16 for insertion under the gingival tissue 30 as shown in FIG. 1 and FIG. 5. The tapered flange 20 permits proper adaptation of restorative material 32, at the gingival or subgingival aspect of the tooth, as shown in FIG. 5.

Each of the pair of wings 16 extends outwardly from one of the corner grooves 22 of the matrix, as best shown in FIG. 4. The corner grooves 22 permit ready movement of the wings with respect to the facial surface. Each wing has an intermediate portion 34 extending between one of the corners 22 and a free end 36 having the adhesive pad 17 on an inner surface 38. Each intermediate portion 34 has a thin cross section to permit interproximal insertion of the wings. Each wing is sufficiently flexible to conform to the contour of the proximal and labial surfaces of the tooth 12. If matrices are used on adjacent teeth at the same time, each wing must be sufficiently thin to permit two wings to pass interproximally. The intermediate portion 34 has a length generally equilavent to the proximal surface of the tooth.

A notch 35 may be formed, as shown in FIG. 5, for accepting the gingiva. Additionally, the intermediate portion 30 and the free end may be angled with respect to each other and to the facial portion to permit proper alignment, as shown in phantom on FIG. 3.

Extending along the inner surface of each of the pair of wings from the lingual surface is the adhesive material 17 as shown in FIG. 1. The adhesive material 17 may be any suitable type which permits adhesion on contact, and in the preferred embodiment, is a strip of resilient material having adhesive on both sides. A sheet 40 of protective material, such as waxed paper, extends along the outer surface of the strip to prevent inadvertent adhesion of the wings. The sheet 40 of protective material is removed prior to final positioning of the matrix about the tooth.

Figure 8:
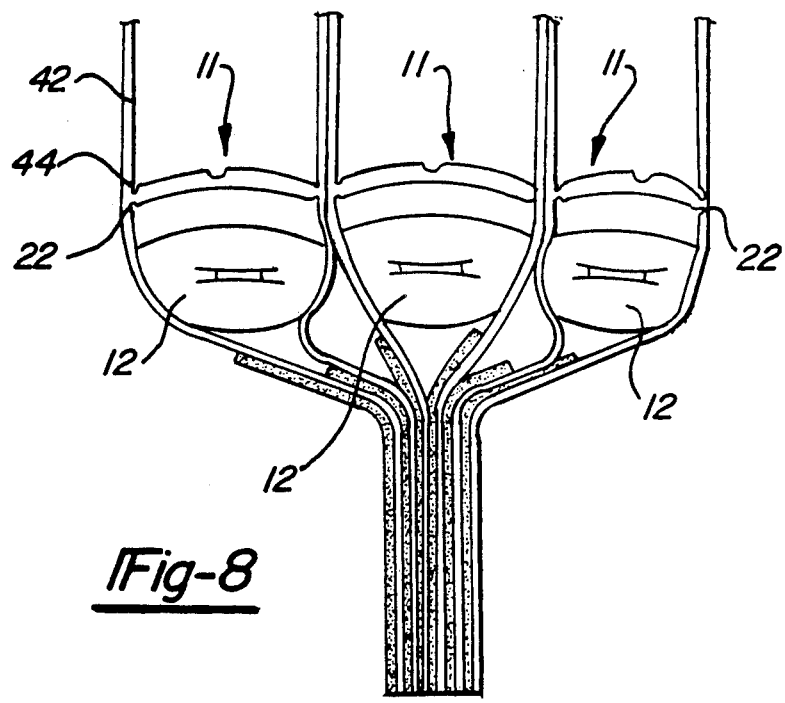
FIG. 8 is a bottom view of three matrices according to the first alternative embodiment of the invention which have been coupled together.

A first alternative embodiment is of a matrix 11 shown in FIGS. 4, 6 and 8. The matrix 11 is formed similarly to matrix 10, but additionally includes a pair of arms 41 extending outwardly from the outer surface 24. The pair of arms 41 extend from corner grooves 44 for grasping by the dentist or technician to facilitate the positioning of the matrix 11.

As shown in FIGS. 7 and 8, an exterior adhesive strip 42 may be positioned on an outer surface of the wing to permit joining of adjacent matrices when several teeth are being restored.

METHOD OF USE

I. Use of the restorative apparatus in conjunction with composite resin restorative material and the like.

To repair deformed, decayed, or damaged teeth, the dentist or technician first selects a matrix having an inner surface 18 corresponding to a labial surface or a desired surface to be formed on the tooth.

The matrix 10 is then positioned with the wings extending proximally and the wedge shaped flange is inserted subgingivally. In the case of the alternative embodiment, the matrix 11 is positioned by grasping one arm and its corresponding wing and manipulating the wing interproximally, then the other arm and its corresponding wing are manipulated into its controlateral interproximal position. Once positioned, the wings of the matrix may be pulled and the matrix is then inspected to determine if any trimming of the matrix is necessary. If no trimming is necessary, the matrix may be pulled labially, so that it fits loosely about the tooth with the flange inserted subgingivally. It is placed in this manner in order to allow room for the introduction and manipulation of any etching, bonding and restorative material to be applied. If trimming is necessary, the matrix is removed from the tooth, trimmed, and then reinserted loosely about the tooth with the flange inserted subgingivally. In the case of the alternative embodiment, the arms 42 of the matrix 11 may be cut off once the matrix is in place about the tooth. The etchant, bonding and restorative material are applied in a manner suitable for the particular compounds that the dentist or technician desires to use. After the restorative material is applied, the wings are pulled tightly and affixed. The wings may be affixed symmetrically as shown in FIG. 6, or offset, as shown in FIG. 8. One or both wings may extend along the lingual to permit restoration of a proximal and/or lingual surface of the tooth. The protective sheet 40 is removed from the adhesive strip. The pair of wings 16 are properly positioned and then pressed together to hold the inner surface to a proper position adjacent to the lingual surface of the tooth as shown in FIG. 6. By affixing the adhesive surfaces together, the matrix is maintained on the tooth, thereby freeing the hands of the dentist or technician for other uses. Additionally, wings of adjacent matrices may be affixed one to another so that multiple teeth can be restored simultaneously, as shown in FIG. 8.

When the wings are pulled tightly, the inner surface 18 of the matrix draws closer to the labial surface of the tooth which causes the restorative material which is trapped between the inner portion of the matrix and the tooth to be molded to the proper shape as determined by the selection of the proper sized matrix. Any excess restorative material is extruded incisally out of this pocket formed by the inner surface of the matrix and the tooth, where it can be easily removed before the restorative material is cured.

The degree of tightness to which the wings are pulled influences the thickness of restorative material that will remain on the labial surface of the tooth. If the dentist or technician desires a thinner amount of material to remain on the labial, he/she simply pulls the wings tighter, causing more of the restorative material to be extruded incisally. The shape of the inner surface 18 of the matrix automatically allows for the restorative material to be thinner at the gingival aspect of the tooth, thereby significantly reducing the risk of the restoration causing gingival irritation.

When the wings are drawn tightly about the tooth on a matrix having an inner surface 18 of the facial portion 14 which is larger than the labial surface or desired surface of a tooth, (see below) then the excess restorative material is extruded incisally and is directed midfacially as the center groove 26 will permit the facial portion of the matrix to flex outwardly from the tooth along this groove. After the restorative material is cured and the matrix is removed, this excess material at the midfacial can be easily and quickly trimmed and polished. The center groove 26 ends at a predetermined distance above the gingival so that excess material is not directed at the gingival aspect of the restoration.

When selecting the proper sized matrix to be used, if a matrix having an inner surface 18 corresponding to a labial surface or a desired surface to be formed on the tooth cannot be found, then a matrix having an inner surface 18 slightly larger mesidoistally than the labial surface or a desired surface to be formed on a tooth should be used. When the wings are drawn tightly about the tooth, the facial portion of the slightly larger matrix will bend at the center groove 26 resulting in a narrower distance between the pair of corners 22 and will produce a proper fit to the labial surface or the desired surface. Additionally, the corner grooves 22 will allow the facial portion of the matrix to flex without disturbing the intermediate interproximal portions of the matrix 34 allowing for these portions to still be maintained about the tooth at the proper angulation.

After the wings are pulled and the matrix is positioned properly, the restorative material can be cured. Most of the restorative materials currently in use are light cured. The matrix is clear and will permit visible and ultraviolet light to pass through the matrix to allow for the curing of photo sensitive material. Also, because the matrix is clear, the restorative material can be viewed to ensure that no voids exist. After the restorative material has cured, the matrix is removed. If necessary, a final forming and shaping of the restorative material may be required. However, the bonding of composite material is accomplished much more quickly than by previously known methods. Also, this method requires significantly less shaping, finishing, and polishing time than prior methods and provides more proper contour of the restorative material, including the contour of the interproximal areas. Also, this method allows an easy way to treat multiple teeth simultaneously and effectively.

II. Use of the restorative apparatus in conjunction with preformed veneers.

The matrix is selected and positioned about the tooth loosely with the flange inserted subgingivally before the etching and bonding in place of the veneer. The matrix will provide for isolation of the tooth during these procedures. The matrix will prevent saliva, water and other unwanted fluids from contaminating the surface of the tooth, and it will prevent etchant solutions and bonding agents from flowing out of the confines of the matrix and onto the gingiva and adjacent teeth. It will also provide for the proper interproximal spacing between teeth, as it will not allow the bonding agent or cement to flow interproximally between adjacent teeth. Additionally, it will allow for the isolation of multiple teeth so that veneers can be bonded into place on many teeth in less time than present methods allow. Also, because the wings of the matrices adhere to each other as shown n FIG. 6, or one to another, as shown in FIG. 8, the dentist or technician's hands are freed to accomplish other tasks, such as preparation and placement of bonding agents onto the inner surfaces of the veneers.

Having thus described my invention, many modifications thereto will become apparent to those skilled in the art to which it pertains without deviation from the spirit of the present invention as defined by the scope of the appended claims.

I claim:

1. An apparatus for use during restoration of a tooth having a labial surface, a pair of proximal surfaces, and a lingual surface, said apparatus comprising:

a matrix having a facial portion, said facial portion having an anatomically shaped inner surface adjacent to and covering said labial surface of said tooth; and means for pulling said inner surface of said matrix into a position adjacent said labial surface, said means for pulling further comprising at least one interproximal wing attached to and extending from said facial portion.

2. The apparatus of claim 1, wherein said facial portion has a center groove to permit deformation of said inner surface.

3. The apparatus of claim 1, wherein said matrix has an outer surface extending between a pair of corner grooves for permitting said at least one wing to bend.

4. The apparatus of claim 1, wherein said matrix is formed of clear material.

5. The apparatus of claim 1, wherein said at least one wing comprises a pair of wings extending from said facial portion.

6. The apparatus of claim 5, wherein said means for securing comprises at least one adhesive strip mounted to an inner surface of at least one of said pair of wings.

7. The apparatus of claim 5 further comprises said pair of wings extending in a spaced apart parallel relationship from said facial portion.

8. The apparatus of claim 1 further comprising means for joining a pair of wings of one matrix to one wing of an adjacent matrix.

9. The apparatus of claim 1, wherein said matrix further comprises a pair of arms extending in a direction away from an outer surface of said facial portion.

10. The apparatus of claim 1, wherein said at least one interproximal wing is dimensioned to permit insertion of two wings interproximally adjacent teeth.

11. The apparatus of claim 1, wherein said facial portion has means for pivoting said facial portion to and away from said labial portion of said tooth to permit application of said restorative material.

12. A method for restoring a labial surface of a tooth forming an anatomically contoured inner surface on a matrix, said method comprising the steps of:
  forming an anatomically contoured inner surface on a matrix having an interproximal wing;
  applying restorative materials to said labial surface of said tooth;
  pulling said interproximal wing lingually to draw said anatomically contoured inner surface against said restorative material on said surface of said tooth;
  molding restorative material between said inner surface and said surface of said tooth;
  curing said restorative material; and
  removing said matrix from said tooth.

13. The method of claim 12 further comprising the step of affixing a pair of wings of said matrix together to secure said matrix to said teeth.

14. The method of claim 12 further comprising the step of extruding excess restorative material incisially from said matrix.

* * * * *